United States Patent [19]

Rodgers et al.

[11] 4,065,371

[45] Dec. 27, 1977

[54] ELECTROCHEMICAL CARBON METER

[75] Inventors: Douglas Noss Rodgers, San Jose; Prodyot Roy, Saratoga, both of Calif.

[73] Assignee: General Electric Company, San Jose, Calif.

[21] Appl. No.: 616,941

[22] Filed: Sept. 26, 1975

[51] Int. Cl.$^2$ .............................................. G01N 27/46
[52] U.S. Cl. ............................................... 204/195 R
[58] Field of Search ............... 204/1 K, 195 P, 195 R; 324/29

[56] References Cited

U.S. PATENT DOCUMENTS

| | | | |
|---|---|---|---|
| 3,679,551 | 7/1972 | Kolodney | 204/1 K |
| 3,700,568 | 10/1972 | Fuhrman | 204/1 K |
| 3,715,296 | 2/1973 | Salzano et al. | 204/195 R |
| 3,769,189 | 10/1973 | Long | 204/195 R |
| 3,865,709 | 2/1975 | Roy et al. | 204/195 R |

OTHER PUBLICATIONS

M. F. Roche et al., Report No. ANL-8017, Argonne National Lab., pp. 5-8, Dec. 1973.

W. E. Ruther et al., Nuclear Technology, vol. 21, pp. 75-78, Jan. 1974.

F. J. Salzano et al., Nuclear Technology, vol. 10, pp. 335-347, Mar. 1971.

*Primary Examiner*—G. L. Kaplan
*Attorney, Agent, or Firm*—Ivor J. James, Jr.; Sam E. Laub; Harold H. Green, Jr.

[57] ABSTRACT

An electrochemical carbon meter is described which is especially useful for measuring the concentration of carbon in liquid sodium. The meter includes a carbon activity gas having a known ratio of carbon monoxide to carbon dioxide contained within a chamber as an intermediary between a diffusion membrane in contact with the sodium and an electrochemical cell. A calcium carbonate fixing compound is also located within the chamber for maintaining the concentration of carbon dioxide therein at a predetermined level. The chamber is fixed to the end of a probe tube which supports the same fully surrounded by liquid sodium to be maintained thereby at a uniform temperature.

14 Claims, 2 Drawing Figures

ELECTROCHEMICAL CARBON METER

BACKGROUND OF THE INVENTION

The present invention relates to an electrochemical meter for measuring the concentration of carbon within a fluid and, more particularly, to such a device which is quite reliable and accurate and is especially designed to measure the concentration of carbon in molten sodium.

It is desirable for various purposes to be able to measure the concentration or activity of carbon in a fluid, such as in a liquid metal or high temperature gas used in an industrial process or commercial equipment. For example, it is quite important to be able to monitor the activity of carbon in the molten sodium heat transfer loops of liquid metal, fast breeder fission reactors. The carbon activity in the sodium is a measure of the detrimental carbonization and decarbonization of the piping, heat exchangers, etc., in contact with the molten sodium.

Various types of carbon activity meters have been designed to measure the activity of carbon in molten sodium. Reference is made to Report No. ANL-8017 available from N.T.I.S., U.S. Department of Commerce, 5285 Port Royal Road, Springfield VA. 22151, for examples of meters designed for this purpose. As will be seen, many of such meters are of the so-called diffusion type. Such meters rely on the diffusion of free carbon from the sodium into a gas stream for later analysis to determine the amount of carbon picked up thereby. One of the primary difficulties with such meters is that a relatively cumbersome gas phase analysis procedure is required for their use. Moreover, such diffusion meters are only capable of indicating changes in the carbon activity, rather than provide absolute measurements of the amount of carbon activity. Other meters have been designed which are, in effect, electrochemical cells. Most electrochemical carbon meters, as they are called, use molten alkali metal carbonate as an electrolyte. Such designs are typically unacceptable because of the corrosive nature of the carbonate electrolyte and their inability to detect carbon activity at the levels which are generally found in liquid sodium-stainless steel systems.

In order to circumvent some of the above problems, an electrochemical carbon meter has been designed which uses a carbon activity gas as an intermediary between the molten sodium and an electrochemical cell. Such meter is fully described in the W. Ruther et al paper appearing in *Nuclear Technology*, Volume 21, page 75, (1974). While this meter circumvents some of the problems of meters of earlier designs, it has its own difficulties. A major one is that the intermediary gas activity is affected by variables other than the amount of carbon which is diffused into it from the sodium. While attempts have been made to correct the inaccuracies inherent in it in view of such uncontrolled variables by, for example, periodically adjusting the total pressure of the gas, the necessity of such corrective factors has made use of the meter for continuous on-line carbon activity monitoring unwieldy.

SUMMARY OF THE INVENTION

The present invention is an electrochemical meter for measuring the concentration of carbon within a fluid which provides absolute and accurate measurements of carbon activity within a fluid, while yet being simple and capable of use as a continuous monitoring device.

In its basic aspects, the electrochemical meter includes a chamber to be placed within the fluid having the carbon concentration to be measured with the interior of such chamber physically separated from the body of the fluid. The wall of the chamber includes a diffusion membrane transparent to any free carbon within the liquid, and a carbon activity gas which will react and equilibrate with any free carbon diffusing into the chamber, fills the chamber. An electrochemical cell is also located within the chamber physically separated from the fluid. Such electrochemical cell is adapted to generate an electrical potential proportional to the amount of carbon activity in the carbon activity gas.

As a particularly salient feature of the instant invention, it includes a fixing compound within the chamber for maintaining the concentration of the carbon containing compounds in the carbon activity gas therein in a known relationship with any variations in such relationship depending only on the amount of free carbon in the carbon activity gas. The result is that variations in such relationship will be proportional to the amount of free carbon diffusing into the chamber through the diffusion membrane. Thus, measurement of the carbon activity in the gas will provide an accurate indication of the amount of free carbon diffusing into the chamber, and hence, the concentration of carbon in the sodium.

As another important feature of the invention, the volume of the chamber containing the carbon activity gas is fully surrounded, essentially by the fluid. If the temperature of the fluid remains generally uniform around such chamber, the result is that the fluid, e.g., sodium, will maintain the temperature of the activity gas generally uniform throughout its volume. Thus, variations in the carbon activity of the gas due to temperature variations or movement in it caused by convection currents will be prevented.

A carbon activity gas which is particularly useful in the electrochemical cell is a mixture of carbon monoxide and carbon dioxide. A fixing compound which is particularly suitable for use with such a mixture is an alkaline earth carbonate, such as calcium carbonate, which fixes the partial pressure of the carbon dioxide. The chamber is fully submerged within the fluid as desired to maintain its temperature uniform, by being supported adjacent the end of a probe tube which is adapted to be inserted into the fluid.

While various electrochemical cells are usable as part of the invention, one major advantage of the invention is that it enables a cell having a molten alkali metal carbonate electrolyte to be used without the corrosion or contamination problems normally associated therewith. An oxygen activity cell is also usable for the electrochemical cell included as part of the invention, if the carbon activity gas is one, such as the aforementioned mixture of carbon monoxide and carbon dioxide, whose oxygen activity also varies proportional to the amount of free carbon therein. In general, oxygen activity electrochemical cells are more accurate and reliable than carbon activity cells and, thus, these advantages of an oxygen activity cell can be transmitted to a measurement of carbon by an electrochemical carbon meter incorporating the invention.

The invention includes other features and advantages which will be described or will become apparent from the following more detailed description of preferred embodiments.

BRIEF DESCRIPTION OF THE DRAWING

With reference to the accompanying single sheet of drawing.

DETAILED DESCRIPTION OF THE PREFERRED EMBODIMENTS

Figure 1:
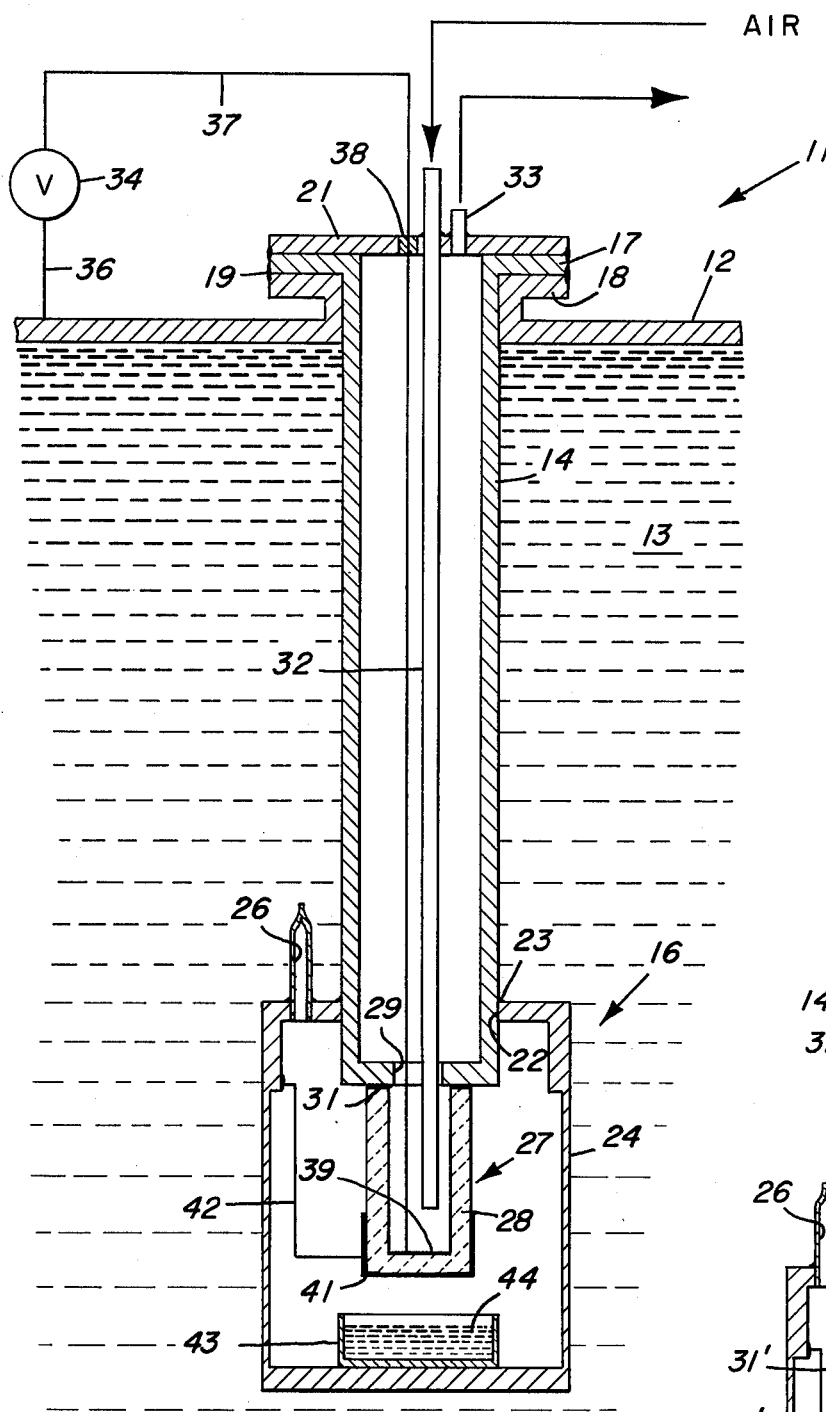
FIG. 1 is a schematic sectional view illustrating a preferred embodiment of the invention.

With reference first to FIG. 1 of the drawing, a preferred embodiment of the electrochemical carbon meter of the invention is generally referred to by the reference numeral 11. Such device is shown extending through the wall 12 of piping containing the flow of a fluid, such as the molten sodium 13. In this connection, the device includes an elongated probe tube 14 of a material which will not be corroded by the fluid whose carbon concentration is to be measured. As illustrated, such probe tube supports adjacent its lower end a chamber 16 submerged within the molten sodium. The upper end of the probe tube 14, i.e., that end on the exterior side of wall 12, is provided with an outwardly projecting circumferential flange 17. Such flange mates with a corresponding flange 18 on the wall 12 circumscribing the piping aperture through which the probe tube extends. Flanges 17 and 18 are suitably secured together, such as by circumferential weld 19 as shown. Also, a top seal plate 21 closes the upper end of the tube 14 and seals its interior from the ambient atmosphere for reasons which will be described.

Chamber 16 has several functions. For one, such chamber defines a volume within its interior which is physically separated from the body of the fluid 13. That is, the chamber 16 is in the form of a closed hollow cylinder having an axial aperture 22 in its top wall through which the probe tube 14 fits in close physical contact. Chamber 16 is secured to tube 14 via a suitable securance, such as a weld 23, at the joint between the tube and the chamber. It should be noted that it is important in order to prevent contamination of the interior of the chamber that the securance between the chamber and tube be fluid tight.

The wall of the chamber 16 includes a diffusion membrane which is transparent to any free carbon within the sodium 13. To this end, the wall includes, as is illustrated, a cylindrical section 24 of its side wall which is sufficiently thin, e.g., 10 mils, to permit the ready diffusion into the interior of the chamber of free carbon within the sodium. The material from which the chamber wall is made must be transparent to carbon at certain thicknesses. It also must have the structural strength and stability with respect to the flow and material of the fluid to be self-supporting and have a sufficiently long life within the environment of the fluid to be practical. When the fluid is molten sodium, as in this case, a suitable material is nickel. It should be noted that nickel is transparent to hydrogen, as well as carbon, and nickel is therefore only suitable as a practical matter when the fluid is one containing insignificant amounts of hydrogen, e.g., less than $10^{-2}$ torr partial pressure of hydrogen.

The chamber 16 also contains a carbon activity gas made up of a plurality of carbon containing compounds which will react with any free carbon therein and equilibrate. Suitable, and preferred, carbon containing compounds for this purpose are carbon monoxide (CO) and carbon dioxide ($CO_2$). That is, the interior of said chamber is filled with a gas mixture having known concentrations of carbon monoxide and carbon dioxide. To this end, a sealed pinch tube 26 is provided for the initial filling of the interior of the chamber with the carbon activity gas.

As is known, free carbon which diffuses into the interior of the chamber 16 through the membrane 24 will react and equilibrate with the carbon monoxide and carbon dioxide according to the following reaction:

1. $C + CO_2 \rightleftharpoons 2 CO_{(g)}$

The equilibrium constant for the reaction is:

$K_1 = P_{CO}^2/(P_{CO_2} \times a_c)$ or

2. $a_c = P_{CO}^2/(P_{CO_2} \times K_1)$, wherein:

$P_{CO}$ = Partial Pressure of Carbon Monoxide
$P_{CO_2}$ = Partial Pressure of Carbon Dioxide
$K_1$ = Equilibrium Constant
$a_c$ = Carbon Activity In the embodiment of FIG. 1, the carbon activity is indirectly measured by measuring the electrical potential generated by an electrochemical oxygen cell due to changes in the oxygen activity in the carbon activity gas mixture caused by corresponding changes in the carbon activity. To this end the chamber 16 further contains an oxygen activity electrochemical cell generally referred to by the reference numeral 27. Such cell includes, as is shown, a cup 28 of a solid electrolyte material, such as zirconia ($ZrO_2$) stabilized with between about 10 and 15 percent of calcium oxide (CaO). As illustrated, the solid electrolyte cup 28 is secured to the bottom wall of the probe tube 14 surrounding a central aperture 29 therein by a braze 31 or the like.

The oxygen activity electrochemial cell 27 further includes a gas reference electrode having a known oxygen activity. That is, a gas supply tube 32 extends from a suitable gas source (not shown) through the seal plate 21 and aperture 29 into the interior of the cup 28. In accordance with conventional practice, a gas having a known oxygen concentration or activity, such as air which has a partial pressure of oxygen equal to 0.21 atm., is introduced continuously through the tube 32 into the cup 28 for contact with the inner side thereof. The pressure of the air is maintained constant via an exhaust nipple 33 which is suitably connected to an appropriate exhaust means, such as an air pump. It should be noted that the cup 28 acts not only as a solid electrolyte, but also to separate the gas reference electrode from the carbon activity gas within the chamber 16.

The oxygen activity within the carbon activity gas mixture is determined by the following equation:

3. $CO_{(g)} + \frac{1}{2} O_{2(g)} \rightleftharpoons CO_{2(g)}$

The equilibrium constant for this reaction is:

4. $K_3 = P_{CO_2}/(P_{CO} \times P_{O_2}^{\frac{1}{2}})$ or $P_{O_2}^{\frac{1}{2}} = P_{CO_2}/(P_{CO} \times K_3)$ wherein:

$P_{O_2}$ = Partial Pressure of Oxygen $P_{CO_2}$ = Partial Pressure of Carbon Dioxide Pco = Partial Pressure of Carbon Monoxide K₃ = Equilibrium Constant for the Reaction.

The electrochemical cell generates an EMF proportional to the partial pressure of oxygen in the carbon activity gas according to the following equation:

$$EMF = \frac{RT}{4F} \log_e \frac{P_{O_2}\frac{CO}{CO_2}}{P_{O_2} \text{ ref}} \quad (5)$$

where:
R = Gas Constant
T = Temperature
F = Faraday Constant
$P_{O_2}$ = Oxygen Partial Pressure To obtain a measurement of such electromotive force, a high impedance (e.g., 10 megohm) voltmeter which will draw insufficient current to affect the readings is connected via the liquid sodium between the reference electrode and the electrical potential generated at the exterior of the solid electrolyte 28. That is, a high impedance voltmeter 34 has one of its terminals connected via a lead 36 to the wall 12 of the liquid sodium piping, which piping will be at the same potential as liquid sodium therein. The other terminal of the voltmeter is connected to a lead 37 of platinum or the like which extends through the seal plate 21 via an insulator 38, and therebeyond into contact with reference electrode plating 39 on the interior side of the solid electrolyte 28. To complete the electrical circuit on the sodium side of the cell, electrode plating 41 on the exterior of the solid electrolyte is connected via a lead 42 to the metal wall of the chamber 16. Because such chamber is in conductive contact with the sodium, the electrode plating 41 is thus maintained at the same potential as such sodium. Thus, the voltage reading on the voltmeter 34 will indicate the electrical potential which is generated across the solid electrolyte 28 by the difference in oxygen activity between the reference electrode gas and the carbon activity gas.

To make the oxygen activity in the carbon activity gas dependent only on the amount of free carbon which diffuses into the chamber through the membrane 24, it is important that the partial pressure of all of the carbon-oxygen compounds in the carbon activity gas be maintained in a known relationship, with any variation in such relationship depending only upon the amount of free carbon which is present in the carbon activity gas. In this connection, as a significant feature of the instant invention, it includes fixing compound means which maintains the concentration of the carbon dioxide in the carbon activity gas at a predetermined level. That is, there is located within the chamber 16 a refractory crucible 43 which contains an alkaline earth carbonate which equilibrates with its reaction products, one of which is carbon dioxide. The preferred alkaline earth carbonate for this purpose is calcium carbonate. Solid calcium carbonate will equilibrate with carbon dioxide as a reaction product according to the following reaction:

6. $CaCO_{3(s)} \rightleftarrows CaO_{(s)} + CO_{2(g)}$

The partial pressure of carbon dioxide within the carbon activity gas can thus be calculated from the thermodynamic data of the above equation. The voltage generated by the oxygen cell indicative of the partial pressure of oxygen will therefore allow the ratio of carbon monoxide to carbon dioxide within the carbon activity gas to be calculated utilizing equation (4) set forth earlier. Once this ratio is known, the desired measurement of the activity of carbon ($a_c$) in the carbon activity gas can be determined with the use of equation (2) above. Since this activity of carbon in the carbon activity gas is in equilibrium with carbon activity in the sodium due to the diffusion membrane 24, the desired activity of carbon within the liquid or molten sodium is obtained. It should be noted that to simplify the above in actual operation, precalculated tables can be provided setting forth the carbon activity, with the temperature of the sodium and the EMF reading on the voltmeter as variables.

Because the activity within the carbon activity gas is temperature dependent, it has been found that for truly accurate readings, such carbon activity gas must be maintained at a generally uniform temperature throughout its volume. As another salient feature of the instant invention, the chamber 16 is adapted to maintain such gas at a generally uniform temperature. That is, as is illustrated, the positioning of the chamber on the end of a probe tube will result in the volume of the chamber containing the carbon activity gas being essentially fully surrounded by the sodium. Although the temperature of sodium flowing by the meter might vary over a period of time, at any given time such sodium will be at a generally uniform temperature around the chamber. That is, there essentially will be no significant temperature differential at any time between the sodium in contact with one portion of the chamber and the sodium in contact with any other portion thereof. Thus, the temperature of the carbon activity gas throughout its volume will be maintained generally uniform by uniform thermal exchange with the sodium. Temperature differentials and consequent movements due to convection currents in the carbon activity gas will be prevented.

Figure 2:
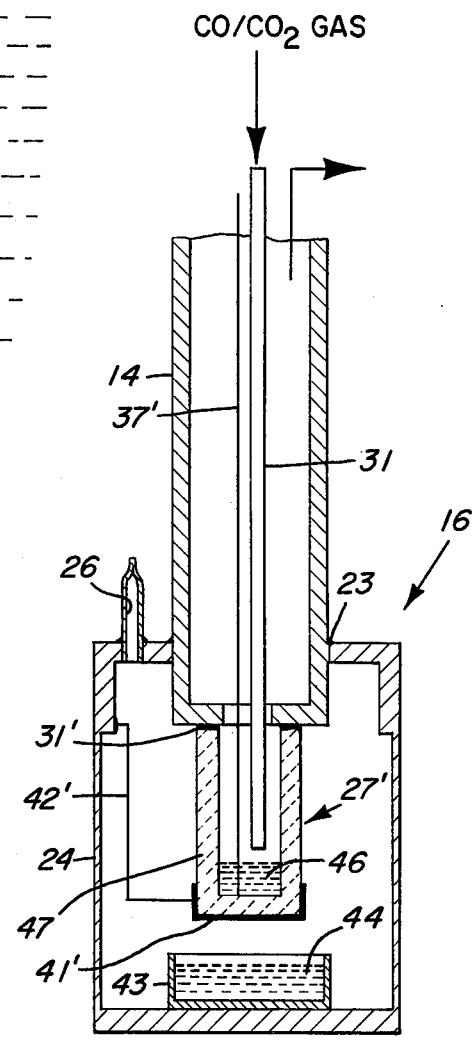
FIG. 2 is a partial sectional view illustrating those aspects of another preferred embodiment of the invention which differ from aspects of the embodiment illustrated in FIG. 1.

As mentioned previously, various different types of electrochemical cells can be used in combination with the other aspects of the invention with equally as good results. FIG. 2 is directed to an embodiment of the invention utilizing such a different electrochemical cell. Other aspects of the embodiment of FIG. 2 are the same as in the embodiment of FIG. 1 and are therefore referred to by the same reference numerals. With respect to the electrochemical cell, it is referred to by the reference numeral 27' and measures the carbon activity within the carbon activity gas directly rather than indirectly by measuring the oxygen activity thereof. Such cell includes a molten alkali metal carbonate electrode 46 contained in a slightly porous refractory crucible 47 of, for example, alumina or magnesia, capable of containing and supporting the alkali metal carbonate electrolyte 46 while physically separating the reference electrode gas from the carbon activity gas but maintaining electrochemical contact therebetween. The crucible 47 is supported from the end of the probe tube 14 by a metal-ceramic seal or braze 31'. While any of the alkali metal carbonates which are used as electrolytic materials will suffice, it is preferred that the electrolyte be a mixture of at least two of the carbonates selected from the group consisting of sodium carbonate ($Na_2CO_3$); potassium carbonate ($K_2CO_3$); and lithium carbonate ($Li_2CO_3$). The reference electrode in this embodiment is provided by a gas mixture having a known concentration ratio of carbon monoxide and carbon dioxide.

The electrical potential generated by ionic conduction in the molten alkali earth carbonate electrolyte 46 is measured in the same way as in the previously described embodiment. However, the lead 37' is most desirably of a material, such as gold, which will be inert to the alkaline earth carbonate. Moreover, such lead need only contact such molten carbonate, rather than have its end provided with a reference electrode plating. The electrode plating 41' and lead 42' on the exterior side of the crucible 47 is also most desirably gold to prevent unwanted reactions with the carbonate.

With the embodiment of FIG. 2, the electrical potential generated by the electrical chemical cell will provide a direct measurement of the ratio of carbon monoxide to carbon dioxide in the carbon activity gas, relative to the known ratio of the same gases within the reference electrode, according to the following equation:

$$EMF_{volt} = \frac{RT}{2F} \log_e [ (\frac{P_{CO}}{P^2_{CO_2}}) \text{ref} (\frac{P^2_{CO_2}}{P_{CO}}) ] \quad (7)$$

with the notations being the same as those set forth for equation (5) above.

The partial pressure of carbon dioxide is also fixed in this embodiment by the presence of calcium carbonate 44 and its reaction products inside the chamber 16. The result is that the activity of carbon within the carbon activity gas, and hence the activity of carbon within the sodium, can be calculated using equation (2) set forth above.

It will be recognized that this embodiment of the invention includes many of the advantages inherent in the use of a molten alkali metal carbonate as an electrolyte, while circumventing the disadvangtages thereof. That is, because the molten carbonate is contained within a refractory crucible and is separated from any physical contact with the carbon transparent membrane, corrosion and contamination by the same is prevented.

Although the invention has been described in connection with preferred embodiments thereof, it will be appreciated by those skilled in the art that various changes and modifications can be made without departing from its spirit. For example, while the preferred embodiments described are especially adapted for use in measuring the carbon activity in molten sodium, the principles of the electrochemical meter are also adaptable to be used in meters designed for measuring carbon activity in other fluids, including gases. It is, therefore, intended that the coverage afforded applicants be limited only by the following claims and their equivalent language as it defines the spirit of the invention.

We claim:
1. An electrochemical meter for measuring the concentration of carbon within a fluid comprising:
   a. a probe having attached at one end
   b. a chamber to be placed within the fluid having the carbon concentration to be measured with the interior of said chamber being physically separate from said fluid and the wall of said chamber including a diffusion membrane transparent to any free carbon within said fluid;
   c. a carbon activity gas within said chamber containing a plurality of carbon containing compounds which will react with any free carbon therein and equilibrate;
   d. an electrochemical cell within said chamber being physically separate from said fluid, said electrochemical being capable of generating an electrical potential proportional to the amount of carbon activity in said carbon activity gas; and
   e. fixing compound means in said chamber for maintaining a level of concentration of one of said carbon containing compounds in said carbon activity gas with any variations in such concentration depending only on the amount of free carbon in the gas whereby variations in the carbon activity in said gas are proportional to the amount of free carbon diffusing into said carbon activity gas through said diffusion membrane.

2. The electrochemical meter of claim 1 for measuring the concentration of carbon within a fluid wherein said chamber is adapted to maintain the carbon activity gas therein at a generally uniform temperature throughout its volume, whereby convection currents within said gas are prevented.

3. The electrochemical meter of claim 1 for measuring the concentration of carbon within a fluid wherein said electrochemical cell within said chamber includes a molten alkali metal carbonate electrolyte and a reference electrode provided by carbon containing gas compounds.

4. The electrochemical meter of claim 3 for measuring the concentration of carbon within a fluid wherein said electrochemical cell further includes a refractory crucible containing and supporting said alkali metal carbonate electrolyte while physically separating said reference electrode gas from said carbon activity gas within said chamber but maintaining electrochemical contact therebetween.

5. The electrochemical meter of claim 1 for measuring the concentration of carbon within a fluid wherein said carbon activity gas is a mixture of carbon monoxide and carbon dioxide, and said fixing compound means includes an alkaline earth carbonate.

6. The electrochemical meter of claim 5 for measuring the concentration of carbon within a fluid wherein said alkaline earth carbonate fixing compound is calcium carbonate which fixes by dissociation the partial pressure of carbon dioxide within said carbon activity gas.

7. The electrochemical meter of claim 5 for measuring the concentration of carbon within a fluid wherein said electrochemical cell is an oxygen activity electrochemical cell which measures the activity of the oxygen within said carbon activity gas.

8. The electrochemical meter of claim 7 for measuring the concentration of carbon within a fluid wherein said oxygen activity electrochemical cell includes a gas reference electrode having a known oxygen activity and a solid electrolyte separating said gas reference electrode from said carbon activity gas.

9. An electrochemical meter for measuring the concentration of carbon within a fluid which is at a generally uniform temperature at the location of said meter comprising:
   a. a probe having attached at one end
   b. a chamber to be placed within the fluid having the carbon concentration to be measured with the interior of said chamber being physically separate from said fluid and the wall of said chamber including a diffusion membrane transparent to any free carbon within said fluid;
   c. a carbon activity gas within said chamber;

d. an electrochemical cell within said chamber being physically separate from said fluid, said electrochemical cell being capable of generating an electrical potential proportional to the amount of carbon activity in said carbon activity gas;

e. said chamber for containing said carbon activity gas being capable of being substantially surrounded by said fluid when submerged within said fluid whereby the temperature of said gas is maintained generally uniform throughout its volume by said fluid and convection currents therein are prevented; and f. a fixing compound in said chamber being positioned to be in contact with said carbon activity gas for maintaining a level of concentration of one of said carbon containing compounds in said carbon activity gas.

10. The electrochemical meter of claim 9 wherein said fluid whose concentration of carbon is of interest is a non-hydrogen containing fluid and said diffusion membrane of said chamber is of nickel.

11. The electrochemical meter of claim 9 wherein said carbon activity gas consists essentially of a mixture of carbon monoxide and carbon dioxide, and wherein said meter further includes an alkaline earth carbonate fixing compound within said chamber which maintains the concentration of one of said carbon monoxide and carbon dioxide constituents of said mixture at a given value, whereby variations in the carbon activity of the other of said constituents are proportional to the amount of free carbon diffusing into said carbon activity gas through said diffusion membrane.

12. The electrochemical meter of claim 11 wherein said alkaline earth carbonate fixing compound is calcium carbonate which fixes by disassociation the partial pressure of carbon dioxide within said carbon activity gas.

13. The electrochemical meter of claim 12 wherein said electrochemical cell is an oxygen activity electrochemical cell which measures the activity of the oxygen within said carbon activity gas, which cell includes a gas reference electrode having a given oxygen activity and a solid electrolyte separating said gas reference electrode from said carbon activity gas.

14. The electrochemical meter of claim 12 wherein said electrochemical cell within said chamber includes a reference electrode provided by a ratio of carbon containing gas compounds and a refractory crucible containing a molten alkali metal carbonate electrolyte, said refractory crucible physically separating both the said electrolyte and said reference electrode gas from said carbon activity gas within said chamber while providing electrochemical contact between said carbon activity gas and said reference electrode gas.

* * * * *